(12) United States Patent
Hofmann et al.

(10) Patent No.: US 9,482,566 B2
(45) Date of Patent: Nov. 1, 2016

(54) METHOD AND DEVICE FOR LOCALIZATION OF DATA LOGGERS ON SUPPLY LINES WITH A READOUT DEVICE

(71) Applicant: Seba Dynatronic Mess -und Ortungstechnik GmbH, Baunach (DE)

(72) Inventors: Michael Hofmann, Breitengussbach (DE); Harald Schuberth, Breitengussbach (DE)

(73) Assignee: Seba Dynatronic Mess -und Ortungstechnik GmbH, Baunach (DE)

( * ) Notice: Subject to any disclaimer, the term of this patent is extended or adjusted under 35 U.S.C. 154(b) by 640 days.

(21) Appl. No.: 13/685,967

(22) Filed: Nov. 27, 2012

(65) Prior Publication Data

US 2013/0173182 A1    Jul. 4, 2013

(30) Foreign Application Priority Data

Dec. 28, 2011    (DE) .................. 10 2011 122 547

(51) Int. Cl.
| | |
|---|---|
| G06F 19/00 | (2011.01) |
| G01F 1/66 | (2006.01) |
| G06F 17/00 | (2006.01) |
| F17D 5/02 | (2006.01) |
| F17D 5/06 | (2006.01) |

(52) U.S. Cl.
CPC ............... G01F 1/666 (2013.01); F17D 5/02 (2013.01); F17D 5/06 (2013.01); G06F 17/00 (2013.01)

(58) Field of Classification Search
CPC ........... G01F 1/666; G06F 17/00; F17D 5/02
USPC ................... 702/45, 150–155, 182–185, 188
See application file for complete search history.

(56) References Cited

U.S. PATENT DOCUMENTS

| 7,891,246 B2 | 2/2011 | Lander |
| 2005/0279169 A1 | 12/2005 | Lander |
| 2008/0018497 A1* | 1/2008 | Farnham ..................... 340/995.1 |
| 2011/0260917 A1* | 10/2011 | Street et al. ............. 342/357.75 |
| 2013/0030690 A1* | 1/2013 | Witmer ......................... 701/409 |

FOREIGN PATENT DOCUMENTS

| DE | 198 20 783 | 9/1999 |
| DE | 101 44 552 | 2/2004 |
| DE | 10 2005 033 491 | 1/2007 |
| EP | 1 805 492 | 7/2013 |

OTHER PUBLICATIONS

Office Action dated Sep. 28, 2015 in corresponding German Application No. 10 2011 122 547.5 together with English language translation of same.

* cited by examiner

Primary Examiner — Edward Raymond
(74) Attorney, Agent, or Firm — Faegre Baker Daniels LLP

(57) ABSTRACT

A method for the deployment and retrieval of data loggers, which are deployed in a first step at separate locations on a supply network having numerous branching pipelines, e.g. for drinking water, which record, in a second step, at least the flow sounds of the medium flowing at the deployed locations, and which, in a third step, are read out by a vehicle driving past, having a readout device disposed therein, wherein the reading device is allocated a GPS module, and that when the data loggers are deployed at the locations assigned to them on the pipeline, the current GPS locations of the data loggers at said locations are stored in the readout device.

20 Claims, 5 Drawing Sheets

Figure 1:
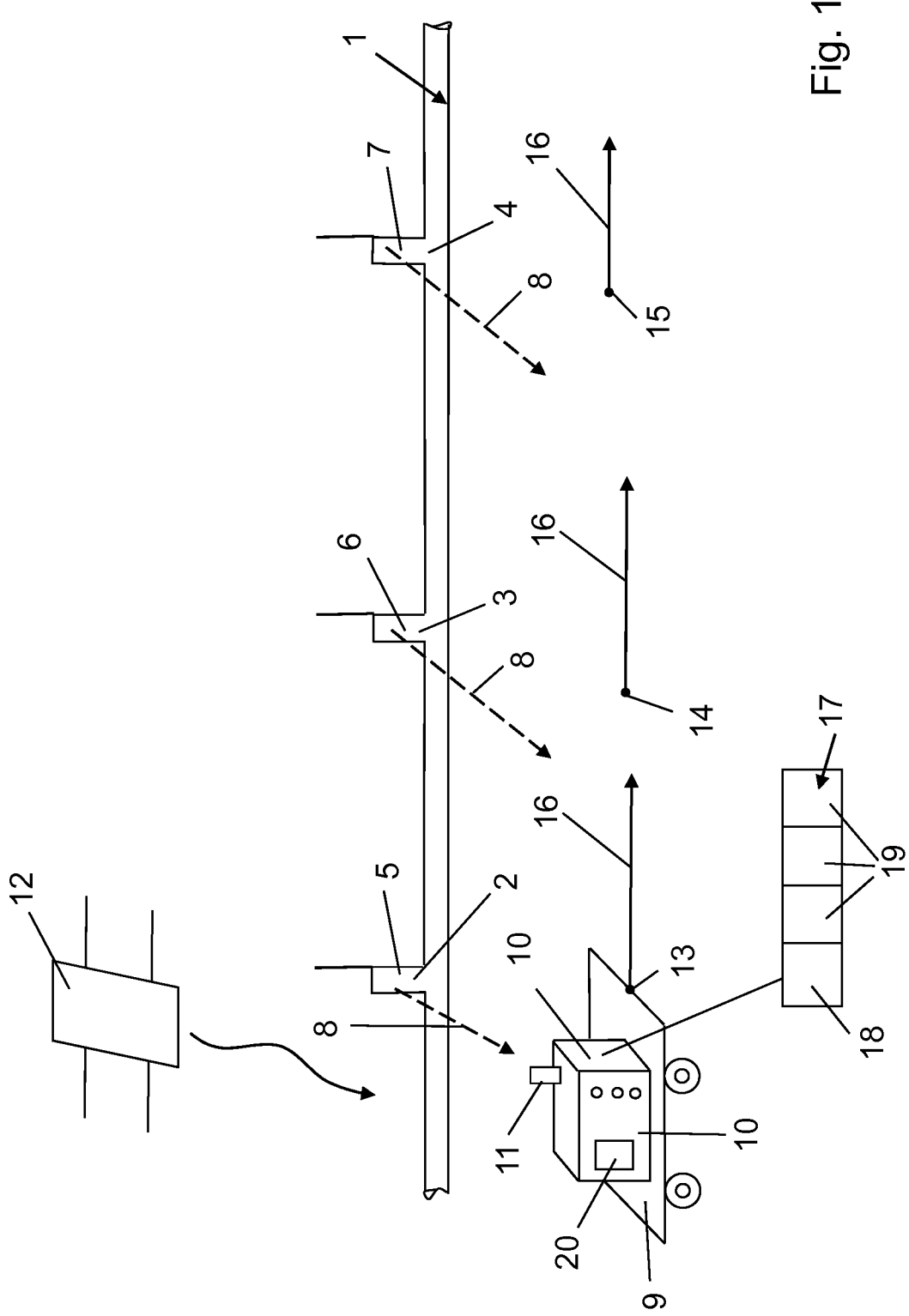

METHOD AND DEVICE FOR LOCALIZATION OF DATA LOGGERS ON SUPPLY LINES WITH A READOUT DEVICE

Data loggers are used for preliminary location of leakages in supply lines, e.g. for drinking water. The data loggers record data which enable a conclusion to be reached regarding a leak location in a pipe.

For this, sound data may be recorded and analyzed. When a set value has been exceeded, a warning or an alarm may be issued. To measure a leak sound, the data logger must be attached to the supply line. For this, the data logger is normally attached by means of a magnet or other attachment method to the supply line at a point that is readily accessible, e.g. a hydrant or shut-off valve.

Because the supply networks extend over a large area, many data loggers must be incorporated in the pipeline network, which can then be monitored on a regular basis.

In a patent that can be traced back to the same applicant, the automatic readout of the data logger while driving past in a vehicle is known. For this, the readout device is disposed in the vehicle, and receives the radio signal emitted by the respective data logger, in which, e.g. the ID number, the data logger No. and the, up until the readout, recorded and stored sound recordings, are contained.

It was however, a disadvantage, that the exact position of the numerous deployed data loggers was not known. To monitor a specific supply network, numerous data loggers are deployed at the locations that are to be monitored in the supply network at positions lying far apart from one another. The deployment locations of the data loggers, until now, could only be recorded on a geographic map, which required a great deal of effort.

If the deployment locations were not correctly recorded on the map, a retrieval of the deployment location and the data logger that had been deployed there was difficult, or even impossible.

If, during the measurement and recording period, a certain data logger, e.g. because of a dead battery, was not functioning, and had discontinued its radio transmission, no radio transmission could be received when driving past, and one assumed, erroneously, that there was no data logger deployed there. For this reason, many data loggers were lost, because their precise location could not be precisely enough located on a street map.

The invention, therefore, assumes the objective of simplifying, and making more reliable, a method for deploying and retrieving data loggers, which have been deployed at separate, widely spaced locations on a supply network.

To attain the assumed objective, the invention is characterized by the technical teachings of the independent Method Claim. The device used for this is the subject matter of the independent Device Claim.

The advantage of the method according to the invention is that for the readout device, only a GPS receiver, without a compass and map resources, is needed. Maps, prone to error and difficult to work with, are no longer needed.

With the readout device according to the invention, "Commander 3," it is possible to store the GPS location of the data logger when it is deployed on the supply line. In order to simplify the retrieval of the data logger, the geographical coordinates are stored with the data logger data in the readout device by means of GPS (Global Positioning System).

As a result, the import to an analysis software, having pipeline network plans or maps, is simplified. In order to facilitate the retrieval of a deployed data logger, the readout device may be used as a navigation tool. Because said device has neither an integrated compass, nor map resources, an alternative solution had to be found.

If the user moves in one direction, the direction of movement can be determined from two GPS locations. To find the data logger, one would like to know in which direction one must walk or drive.

Through the GPS location of the data logger stored in the readout device, and based on the current GPS location of the user, it is known in which compass direction the data logger is located. Unfortunately, one frequently does not know precisely where north is, in order to be able to move directly toward the data logger.

Because one can determine in which compass direction one moves by means of the movement of the readout device, through reading the display screen, one can therefore also determine in which direction the data logger is located. If the direction of movement is depicted in the software of the readout device such that the compass direction in which one is moving is displayed at the top, and an arrow indicates the compass direction in which the data logger is located, the arrow automatically points in the direction in which one, in a satellite image, can find the position (source: Google-Maps) of the deployed data logger.

In order for the retrieval of the data logger to be made possible, a GPS receiver module must be connected to the readout device (Commander). This can either be attached thereto as an additional, external module, or placed in the interior of the housing.

If the GPS location for every data logger, when deployed at the measuring position on the pipeline, is stored, the readout device knows every geographic location, and can re-locate said positions during a search. In addition, these locations can be depicted on a PC using software, in a geographic map. In this manner, the user can readily determine the location of the respective data logger. By this means, the interpretation of the measurement data is significantly simplified.

The fundamental sequence for storing the GPS locations is as follows:

1. Placement of the data logger at the measurement location
2. GPS location of the data logger is stored
3. The data logger records measurement data
4. Navigation to the measurement location having the data logger
5. Readout of the measurement data Additional possibilities:

The readout of the measurement data can also take place through patrolling the data logger in the framework of a search, when said data logger transmits the data sets by radio signal at predetermined intervals.

If the radio signal of a data logger is not received, because, e.g., said data logger is shut down, a warning may be issued via the readout device when the user is located within the transmission range of the data logger, and does not receive said signal.

The stored locations can be extracted by means of a separate software, and converted to a format that can be read by a navigation device for a motor vehicle.

As a result, an optimal route for patrolling the data loggers can be calculated using the map resources in the navigation device. Using the GPS module, one can also store the locations of other devices, needed, e.g., for the construction of a network. In this manner, one can visualize the structure of the network on a map.

The subject matter of the present invention can be derived not only from the subject matter of the individual Claims, but also from combinations of the individual Claims.

All information and characteristics disclosed in the documents, including the abstract, in particular the spatial design depicted in the drawings, are claimed as substantial to the invention, individually, or in combination, insofar as they are novel with respect to the prior art.

In the following, the invention shall be explained in greater detail, based on drawings depicting only one possible embodiment. In this context, other characteristics substantial to the invention, and advantages of the invention, can be derived from the drawings and the description thereof.

Figure 2:
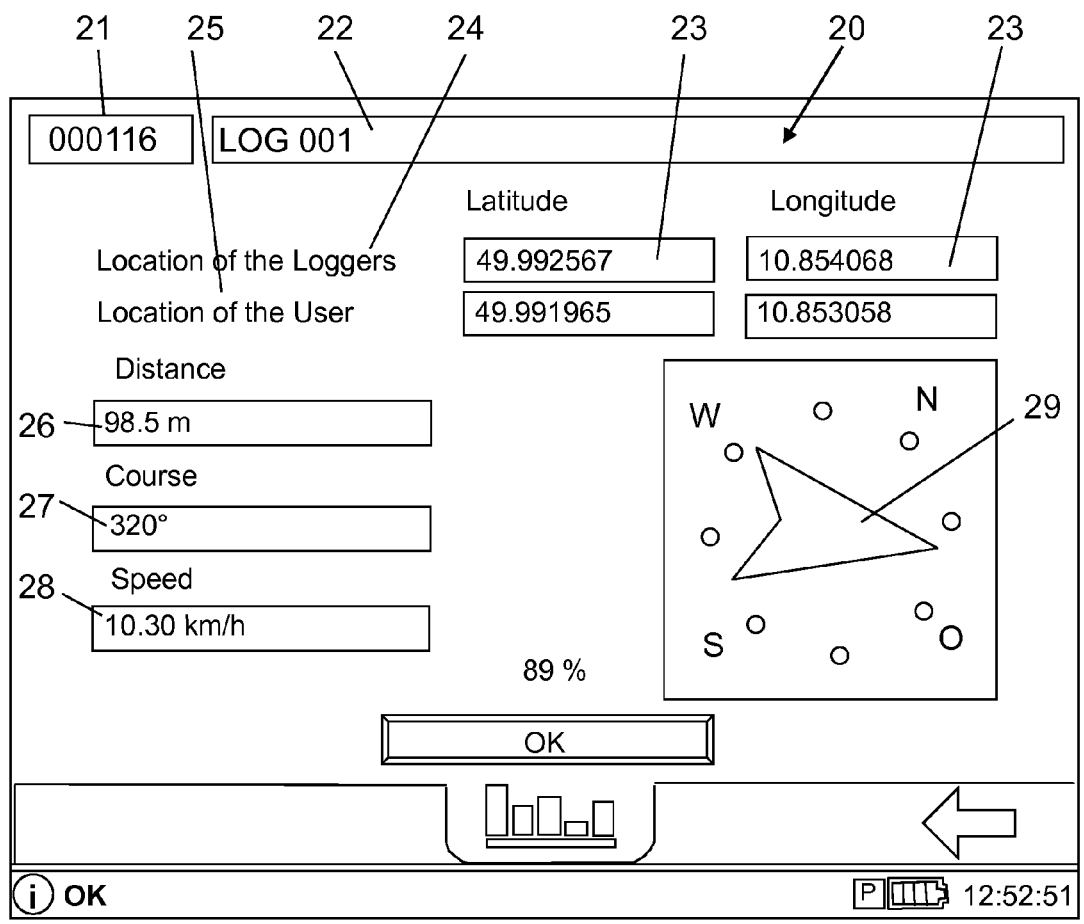
Figure 3:
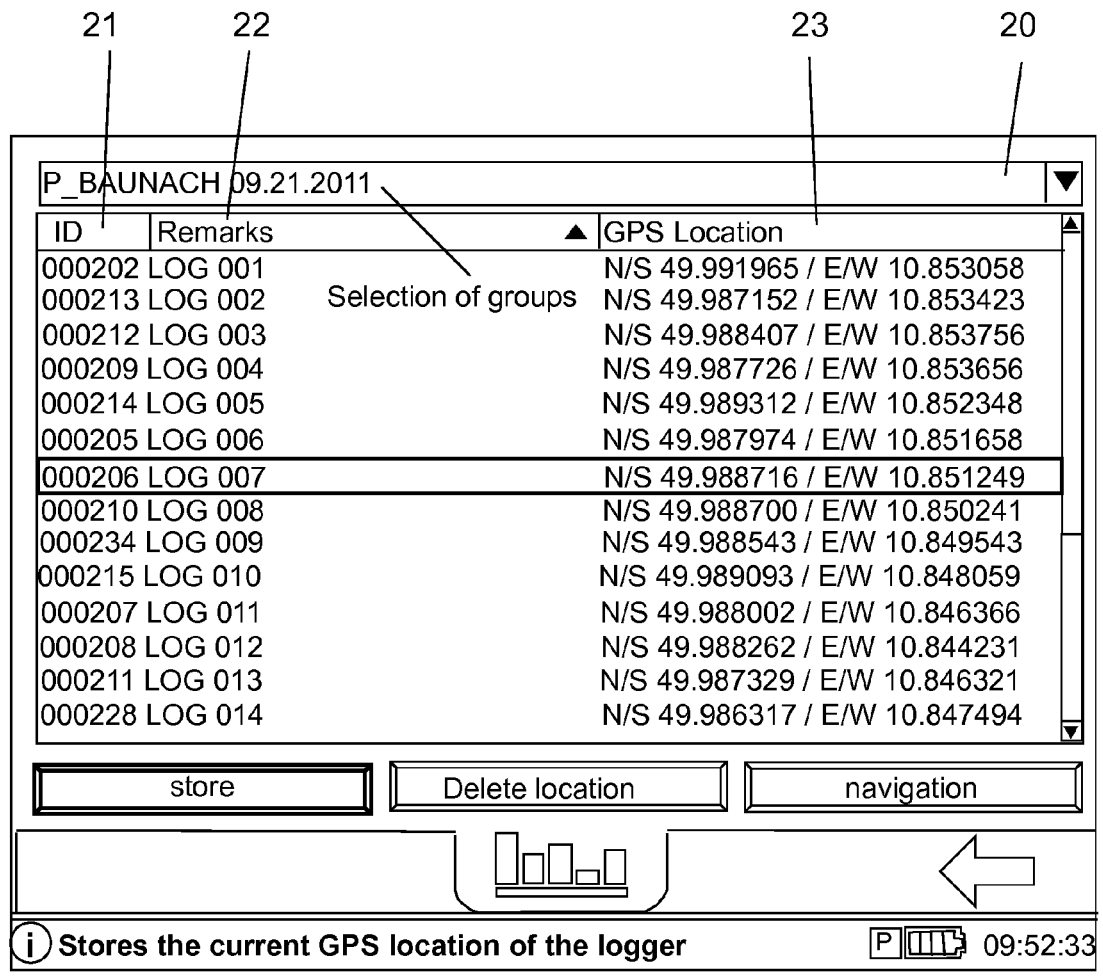
Figure 4:
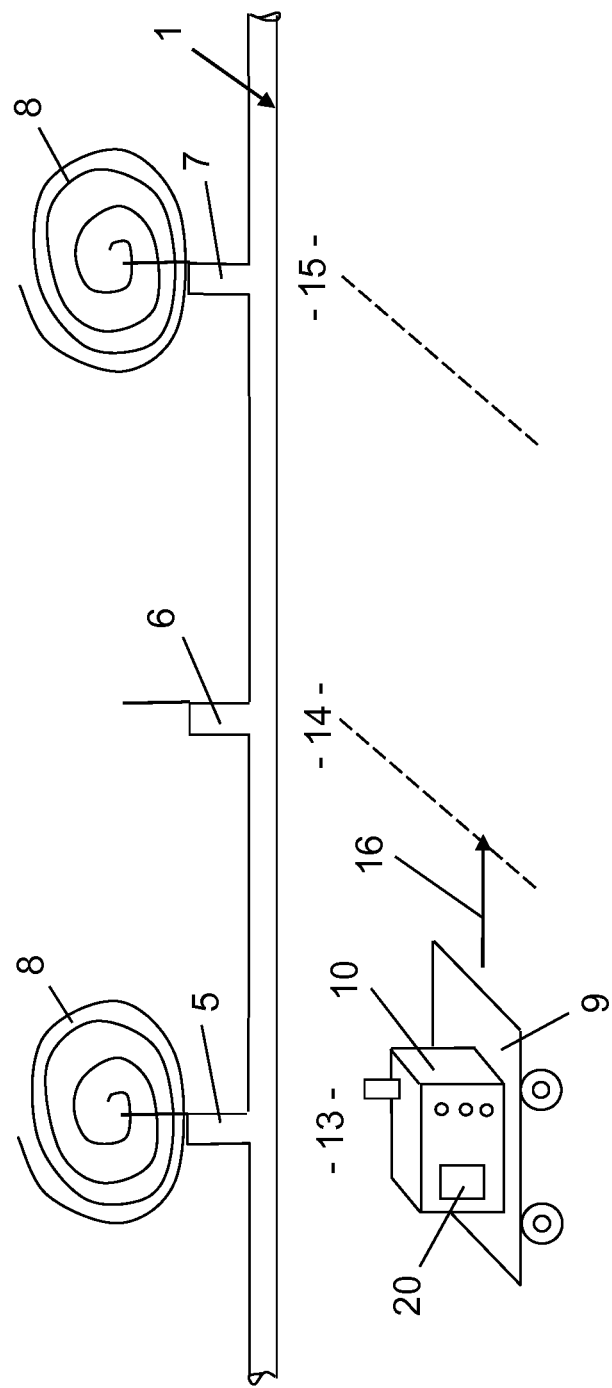
Figure 5:
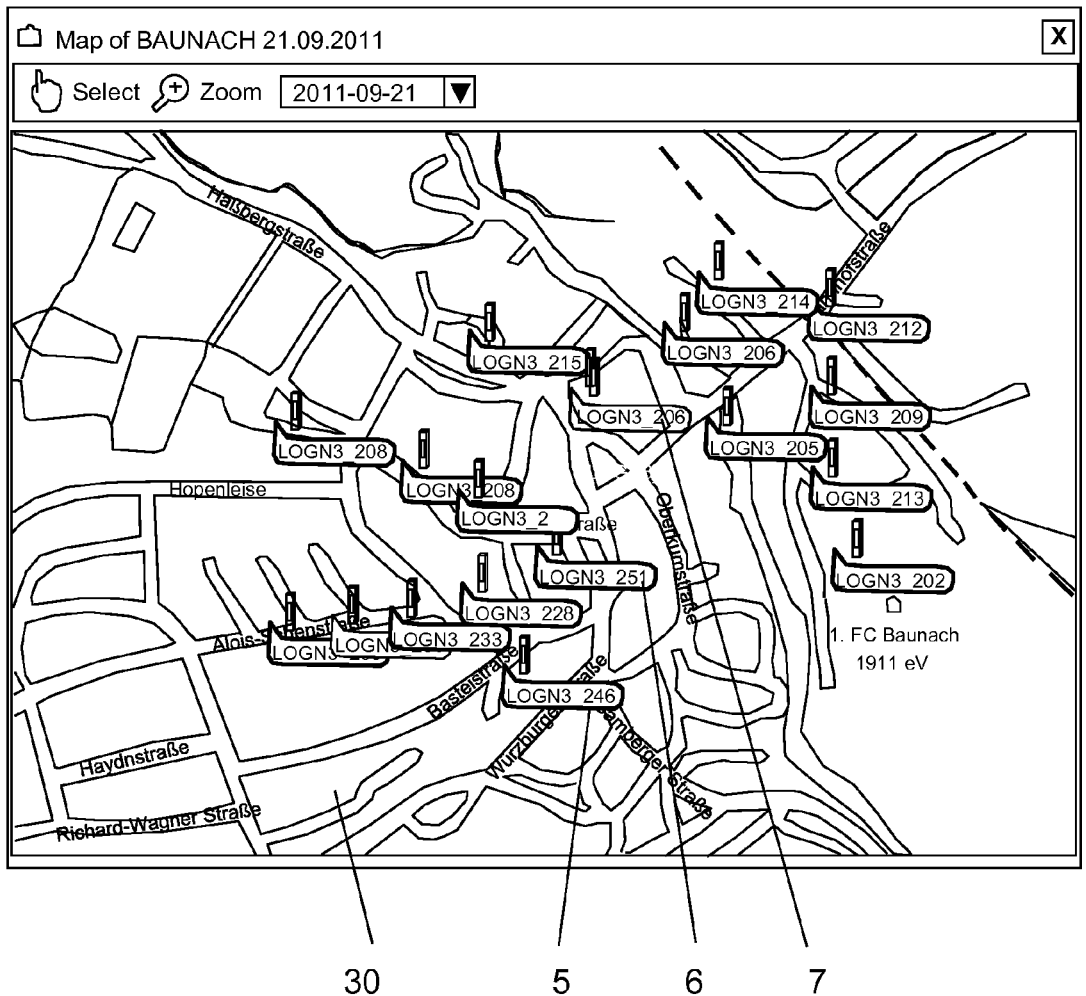

They show:

FIG. 1: in a schematic manner, the measurement drive of a readout device along a pipeline, on which numerous data loggers have been attached, FIG. 2: the screen display of the readout device during retrieval of a data logger, FIG. 3: the screen display of the readout device with the data for the geographic locations of numerous deployed data loggers, FIG. 4: in a schematic manner, an identical depiction to that in FIG. 1, during the readout drive of the readout device along a pipeline, FIG. 5: the depiction of the locations of numerous data loggers on a geographic map.

FIG. 1 shows a measurement drive for a readout device 10, disposed in a vehicle 9, wherein numerous data loggers 5, 6, 7 for monitoring the flow and leakage behavior are attached to a pipeline 1.

In the embodiment example depicted, the data loggers 5, 6, 7 are attached to shut-off valves 2, 3, 4 of the pipeline 1.

The invention, however, is not limited to this. The data loggers can be attached to any locations on the pipeline 1. They contain, in particular, an electronic recording of a digital or analog recording of sound measurements, generated by an incorporated microphone when listening to the pipeline, which are then stored in the data logger.

There is also a series of other measurement functions disposed in the data logger, which are not the subject matter of the present invention. In particular, an ID number 21 and, if applicable, a logger number 22, are also assigned to each data logger, and stored in a data memory 17 characterizing the logger.

Significant to the invention is that during the deployment of a data logger 5, the GPS location of the data logger 5 attached to the shut-off valve 2 is determined in the vehicle 9 from a GPS satellite 12, and stored in the readout device 10. In this manner, each deployed data logger 5, 6, 7 is assigned GPS coordinates 18 in the readout device, which are then stored in the readout device 10. The vehicle 9 travels, for example, from its first location 13, via a route 16 to a second location 14, where, in turn, the data logger 6 is deployed, and at this location, in turn, the GPS coordinates and GPS location 23 for this shut-off valve 3, and the data logger 6 attached thereto, are stored in the readout device 10 as a data block in a memory 17.

The same procedure is then repeated at location 15, such that each data logger 5-7, is assigned individual GPS coordinates, and all data sets are stored in the memory 17 of the readout device 10.

It should also be mentioned that the data loggers 5-7 can be read out via a radio transmission pathway 8 while the vehicle 9 is driving past them.

FIG. 3 shows, as an example, a screen display 20 of the readout device 10, in which each data logger has been assigned a logger number 22 and an ID number 21, wherein each logger number 22 is assigned unique GPS coordinates.

Instead of allocating a logical number as the logger number 22, a name can also be assigned, such that the logger having the number 22 receives the name "Schillerstrasse 5," for example.

FIG. 5 shows that the type and distribution of the logger numbers can be inserted in a geographic map, wherein the logger having a conspicuous measurement result (e.g. due to a leak in the pipeline detected at that location), receives a different color than that of the surrounding loggers, which have stored inconspicuous measurement data.

FIG. 4 shows a so-called readout drive of a readout device 10 disposed on a vehicle 9, where it is visible that by means of the clear assignment of each logger to a GPS location 23 according to the screen display 20 in FIG. 3, and also because each logger is indicated on a geographic map according to FIG. 5 as well, the retrieval of the deployed logger according to FIG. 4 is particularly simple.

The vehicle must only travel along the route 15 of the pipeline 1 corresponding to a previously determined route. The route can be established using the geographic map according to FIG. 5.

It is shown in FIG. 4 that as an error, e.g., a data logger 6 may fail, and then a radio connection and readout is no longer possible with the data logger 6.

Because of the storing of the GPS location 23 for said data logger 6, the readout device 10 would not, however, drive past this location, because it is known to the readout device 10, as a result of the previous storing of each GPS location 23 of each data logger 5, 6, 7, that there must be a data logger 6 located at location 14, even though said data logger remains silent.

In this manner it can be determined, while the readout device is driving past, whether a defective data logger 6 is disposed at this location, which, for some reason, is not transmitting.

FIG. 2 shows a search drive of the readout device 10 of this type to an arbitrary data logger 5, 6, 7, whereby the term "search drive" also means that the readout device 10 can be carried manually, and the carrier of the readout device is then guided precisely to the location of the data logger 5, 6, 7.

During the search drive the readout device 10 is disposed in the vehicle 9, whereby numerous data loggers 5, 6, 7 on a pipeline 1 are to be read for checking the flow and leakage behavior.

For this purpose, the ID number 21 of the relevant logger that is to be retrieved, having the logger number 22, is displayed in an upper bar on the screen display 20 of the readout device 10, and the current geographic location of the logger is displayed in the field lying below this, with the latitude and longitude displayed as the GPS location (target position).

In the horizontal field below this, the current location of the user 25 is also depicted in the form of a GPS location 23, such that the user can navigate from his location 24 to the location of the logger 24.

In the left portion of the screen depiction 20, the distance to the target 26 from the location of the user 25 with respect to the location of the logger 24 is depicted in the upper field, and in the field below this, the course 27 is displayed in terms of angular degrees.

Moreover, the speed 28 of the user's movement toward the logger can also be displayed in the field below this.

In the right-hand field, a directional arrow 29 is depicted as a compass arrow, which shows the direction in which the data logger is located.

By reading the screen display 20, the user is provided therefore with a clear means of navigation for retrieval of the possibly concealed data logger 5-7.

In addition, the user can also make use of the map of the surrounding area depicted in FIG. 5, on which the individual loggers are indicated with their ID numbers.

Loggers having critical measurement values are displayed with different colors.

Even if, therefore, a logger is unable to transmit due to a defect, it is still easy to find in accordance with the depiction in FIG. 4.

In the preceding description it is stated that the GPS location is only stored in the readout device. In another embodiment of the invention it is provided, however, that the GPS location is stored in the data logger when said data logger is deployed on the pipeline. The readout device equipped with the GPS module records the current GPS location of the vehicle 9 at the data logger, and transmits the current GPS location by means of a radio interface to the data logger, in order that it be able to store its own GPS location.

Thus, each data logger knows its own GPS location, and during a readout drive, in which the deployed data loggers are detected based on the GPS locations stored in the readout device, a simplified readout device can also be used, without a GPS module connected thereto. While reading a detected data logger, said data logger also shares its stored GPS location, together with the other data, with the simplified readout device.

| Drawings Legend | |
|---|---|
| 1 | pipeline |
| 2 | shut-off valve |
| 3 | shut-off valve |
| 4 | shut-off valve |
| 5 | data logger |
| 6 | data logger |
| 7 | data logger |
| 8 | radio transmission pathway |
| 9 | vehicle |
| 10 | readout device |
| 11 | GPS module |
| 12 | GPS satellite |
| 13 | location |
| 14 | location |
| 15 | location |
| 16 | route |
| 17 | data memory |
| 18 | GPS coordinates |
| 19 | measurement data |
| 20 | screen display |
| 21 | ID No. |
| 22 | logger No. |
| 23 | GPS location |
| 24 | location of the logger |
| 25 | location of the user |
| 26 | distance to target |
| 27 | course |
| 28 | speed |
| 29 | directional arrow |
| 30 | map of the surroundings |

The invention claimed is:

1. A method for the deployment and retrieval of a plurality of data loggers, comprising deploying in a first step at a plurality of deployed locations on a supply network having numerous branching pipelines recording, with the data loggers, in a second step, at least the flow sounds of a medium flowing at the deployed locations, reading out, in a third step, by a vehicle driving past, having a readout device disposed therein, the data loggers, wherein the readout device comprises a GPS module, the method including the step, when the data loggers are deployed at the locations assigned to them on the pipeline, of storing the current GPS locations of the data loggers at said locations in the readout device.

2. The method according to claim 1, wherein the step of storing the GPS locations of the data loggers in the readout device comprises storing the GPS locations when the data loggers are deployed on the supply line.

3. The method according to claim 2, further comprising using the readout device as a navigation tool during a step of retrieving the deployed data loggers.

4. The method according to claim 2, further comprising depicting the GPS locations of the deployed data loggers stored in the readout device on a geographic map.

5. The method according to claim 2, further comprises the following steps for each of the data loggers:
   1. placing of the data logger at a measurement location;
   2. storing a GPS location of the data logger;
   3. recording, with the data logger, a measurement data;
   4. navigating to the measurement location having the data logger; and
   5. reading out the measurement data.

6. The method according to claim 1, further comprising using the readout device as a navigation tool during a step of retrieving the deployed data loggers.

7. The method according to claim 6, further comprising depicting the GPS locations of the deployed data loggers stored in the readout device on a geographic map.

8. The method according to claim 6, further comprises the following steps for each of the data loggers:
   1. placing the data logger at the measurement location;
   2. storing a GPS location of the data logger;
   3. recording, with the data logger, a measurement data;
   4. navigating to the measurement location having the data logger; and
   5. reading out the measurement data.

9. The method according to claim 1, further comprising depicting the GPS locations of the deployed data loggers stored in the readout device on a geographic map.

10. The method according to claim 9, further comprises the following steps for each of the data loggers:
    1. placing the data logger at the measurement location;
    2. storing a GPS location of the data logger;
    3. recording, with the data logger, a measurement data;
    4. navigating to the measurement location having the data logger; and
    5. reading out the measurement data.

11. The method according to claim 1, further comprises the following steps for each of the data loggers:
    1. placing the data logger at a measurement location;
    2. storing a GPS location of the data logger;
    3. recording, with the data logger, a measurement data;
    4. navigating to the measurement location having the data logger; and
    5. reading out the measurement data.

12. A device for the deployment and retrieval of a plurality of data loggers which are deployed at separate locations on a supply network having numerous branching pipelines, and which record at least the flow sounds of the medium flowing at the deployed locations, and which are capable of being read out by a vehicle driving past, having a readout device disposed therein, wherein the readout device comprises a GPS module, which stores, at least, a stored current GPS location of the deployed data loggers.

13. The device according to claim 12, wherein the readout device comprises at least one display screen, on which at least the stored GPS location of the deployed data logger and a current GPS location of the readout device can be displayed.

14. The device according to claim 13, wherein a direction of the movement of the readout device can be visually displayed using the GPS locations of the data loggers and the readout device.

15. The device according to claim 13, wherein an alarm signal can be generated in the readout device in the case that no radio signal can be received at a stored GPS location of a data logger.

16. The device according to claim 13, wherein a quantity of GPS data stored in the readout device can be converted, and imported onto a conventional motor-vehicle navigation system.

17. The device according to claim 13, wherein the readout device transmits the GPS location of the data logger determined by the readout device, by means of a radio interface, to the respective data logger, which stores the GPS location together with other data, and is capable of being transmitted to the readout device by means of radio signals.

18. The device according to claim 12, wherein an alarm signal can be generated in the readout device in the case that no radio signal can be received at a stored GPS location of a data logger.

19. The device according to claim 12, wherein a quantity of GPS data stored in the readout device can be converted, and imported onto a conventional motor-vehicle navigation system.

20. The device according to claim 12, wherein the readout device transmits the GPS location of the data logger determined by the readout device, by means of a radio interface, to the respective data logger, which stores the GPS location together with other data, and is capable of being transmitted to the readout device by means of radio signals.

* * * * *